US009642887B1

(12) United States Patent
Shah et al.

(10) Patent No.: US 9,642,887 B1
(45) Date of Patent: May 9, 2017

(54) ANTI-BLEPHARITIS COMPOSITIONS AND THEIR USE

(71) Applicants: Shetal Amit Shah, Commack, NY (US); Amit Rajendra Shah, Commack, NY (US)

(72) Inventors: Shetal Amit Shah, Commack, NY (US); Amit Rajendra Shah, Commack, NY (US)

(*) Notice: Subject to any disclaimer, the term of this patent is extended or adjusted under 35 U.S.C. 154(b) by 0 days.

(21) Appl. No.: 15/194,340

(22) Filed: Jun. 27, 2016

Related U.S. Application Data

(62) Division of application No. 14/981,329, filed on Dec. 28, 2015, now Pat. No. 9,439,917.

(51) Int. Cl.
| | |
|---|---|
| *A61P 31/04* | (2006.01) |
| *C07H 15/18* | (2006.01) |
| *A61K 38/16* | (2006.01) |
| *A61P 27/00* | (2006.01) |
| *A61K 8/92* | (2006.01) |
| *A61K 38/08* | (2006.01) |
| *A61K 31/7028* | (2006.01) |
| *A61K 35/06* | (2006.01) |
| *A61K 8/60* | (2006.01) |
| *A61K 8/64* | (2006.01) |
| *A61K 8/96* | (2006.01) |
| *A61K 8/19* | (2006.01) |
| *A61K 36/58* | (2006.01) |
| *A61K 36/9066* | (2006.01) |
| *A61K 36/76* | (2006.01) |
| *A61K 36/64* | (2006.01) |
| *A61K 36/28* | (2006.01) |
| *A61K 36/23* | (2006.01) |
| *A61Q 1/10* | (2006.01) |
| *A61K 8/97* | (2017.01) |

(52) U.S. Cl.
CPC .............. *A61K 38/08* (2013.01); *A61K 8/19* (2013.01); *A61K 8/602* (2013.01); *A61K 8/64* (2013.01); *A61K 8/965* (2013.01); *A61K 8/97* (2013.01); *A61K 31/7028* (2013.01); *A61K 35/06* (2013.01); *A61K 36/23* (2013.01); *A61K 36/28* (2013.01); *A61K 36/58* (2013.01); *A61K 36/64* (2013.01); *A61K 36/76* (2013.01); *A61K 36/9066* (2013.01); *A61Q 1/10* (2013.01); *A61K 2800/70* (2013.01)

(58) Field of Classification Search
None
See application file for complete search history.

(56) References Cited

U.S. PATENT DOCUMENTS

| 7,381,704 B2 | 6/2008 | Owen |
| 9,186,324 B2 | 11/2015 | Friedman |
| 2007/0166267 A1 | 7/2007 | Majewski et al. |
| 2008/0107679 A1* | 5/2008 | Dilallo ............... A61K 8/64 424/195.17 |
| 2014/0079762 A1* | 3/2014 | Perricone ............ A61K 9/127 424/450 |

FOREIGN PATENT DOCUMENTS

WO    WO 2012158591 A1 * 11/2012 ........... A61K 8/0208

OTHER PUBLICATIONS

Avila et al., "Mode of Action of Buddleja Cordata Verbascoside Against *Staphylococcus aureus*", online abstract in Journal of Ethnopharmacology, vol. 66, Issue 1, Jul. 1999, found at http://www.sciencedirect.com/science/article/bii/S0378874198002037 on Dec. 6, 2015, Elsevier Science Ireland Ltd.
Brooks Industries Inc., "NAB Willobark Extract Natural B—Hydroxy Acid", datasheet from Cosmetic Ingredients & Ideas Issue No. 1, Mar. 28, 2000, found at https://www.in-cosmetics.com/_novadocuments/2209 on Dec. 6, 2015.
Majeed et al., "Neem Oil Limonoides: Products Overview", product datasheet from Sabinsa Corporation, 2007, found at http://www.sabinsa.com/products/cosmeceuticals/neem-oil-limonoids/neem-oil-limonoids.pdf on Dec. 6, 2015.
Salman et al., "Antimicrobial Activity of Nigella Sativa Linn. Seed Oil Against Multi-Drug Resistant Bacteria from Clinical Isolates", article in Natural Product Radiance, vol. 7(1), pp. 10-14, 2008, found at https://www.researchgate.net/publication/36448004_Antimicrobial_activity_of_Nigella_sativa_Linn_seed_oil_against_multi_drug_resistant_bacteria_from_clinical_isolates_Nat_Prod_Rad on Dec. 6, 2015.
Sabinsa Corporation, "Sabinsa Corporation Receives Gras Status for Award Winning Branded Ingredient Curcumin C3 Complex", News Release dated Aug. 4, 2009, found at http://www.curcuminoids.com/sabinsa_curcumin_c3_complex_gras_pr_20090804.pdf on Dec. 6, 2015.
Krys Bojanowski, PhD, "Effect of Eye Primer and AzaSite on the growth of *S. aureus* (MIC Study)", Report 485 from Sunny BioDiscovery, Jul. 12, 2011.
Paduch et al., "Assessment of Eyebright (*Euphrasia officinalis* L.) Extract Activity in Relation to Human Corneal Cells Using in Vitro Tests", article in Balkan Medical Journal, Mar. 31, 2014, pp. 29-36, found at http://www.ncbi.nlm.nih.gov/pmc/articles/PMC4115993/ on Dec. 6, 2015.
Herbwisdom.com, Euphrasia/Eyebright benefits, information sheet, 2015, found at http://www.herbwisdom.com/herb-euphrasia.html on Dec. 6, 2015.
Helix Biomedix, OTC Enhancement and Oligopeptide-10 Consumer Products Information, information sheet, Feb. 15, 2015, found at http://helixbiomedix.com/otcenhancement.html on Dec. 6, 2015.
Ichthyol, Ichthyol Pale Product Efficacy and Benefits, information sheet found at http://www.ichthyol.com/ichthyol_pale_efficacy.html on Dec. 6, 2015.

(Continued)

*Primary Examiner* — H. Sarah Park
(74) *Attorney, Agent, or Firm* — Kolisch Hartwell, P.C.

(57) ABSTRACT

Compositions and methods for the prevention and treatment of blepharitis, where the compositions include verbascoside, oligopeptide-10, and sulfonated shale oil, and the preparation of such compositions.

18 Claims, No Drawings

(56) References Cited

OTHER PUBLICATIONS

Ichthyol, Ichthyol Pale Product Formulations and Product Development, information sheet found at http://www.ichthyol.com/ichthyol_pale_formulations.html on Dec. 6, 2015.

Fairhurst et al., "Micro- and Nano- encapsulation of Water- and oil-soluble Actives for Cosmetic and Pharmaceutical Applications", Skin Delivery Systems, Chapter 17, published by Particle Sciences Inc. Downloaded on Dec. 10, 2015 from http://www.particlesciences.com/docs/Skin_Delivery_Systems_Ch17.pdf.

Aug. 2, 2016 Notice of Allowance from US Patent and Trademark Office, in U.S. Appl. No. 14/981,329, which is the application to which this U.S. application claims the benefit of priority.

* cited by examiner

ANTI-BLEPHARITIS COMPOSITIONS AND THEIR USE

CROSS-REFERENCE TO RELATED APPLICATION

This application is a divisional application under 35 U.S.C. §121 of U.S. patent application Ser. No. 14/981,329 filed Dec. 28, 2015, now U.S. Pat. No. 9,439,917, the disclosure of which is hereby incorporated by reference.

TECHNICAL FIELD

The disclosure relates generally to cosmetic compositions, and more specifically to cosmetic compositions useful for the treatment and/or prevention of blepharitis

BACKGROUND

Blepharitis refers to inflammation of the eyelid. It is a common ocular disorder affecting millions of Americans, and may result from any of a continuum of inflammatory disease processes of the eyelid. Blepharitis may be divided anatomically into anterior and posterior blepharitis. Anterior blepharitis refers to inflammation around the eyelashes and follicles, while posterior blepharitis involves the meibomian glands. The pathophysiology of blepharitis involves bacterial colonization of the eyelids, which in turn results in immune-mediated inflammatory damage to the surrounding tissues.

Sufferers of blepharitis typically present with various complaints including burning, watery eyes, foreign body sensation, red eyelids, red eyes, pain and blurry vision. A physical examination of patients with blepharitis can often show a loss of eyelashes, the plugging of the meibomian glands, and/or infection of the conjunctiva. Also, the irritation that blepharitis causes can often lead to dry eyes. If it is severe enough, blepharitis may even affect the cornea, causing marginal infiltrates, marginal ulcers, and pannus formation.

Ophthalmologists often see female patients wearing heavy cosmetics that also complain of the symptoms of blepharitis. In such situations, even though the patients are advised to stop wearing the cosmetics they typically refuse, in order to maintain their desired appearance.

What is needed are formulations that may be useful for treating or preventing blepharitis, and in particular cosmetic formulations that have anti-bacterial and anti-inflammatory properties.

SUMMARY

The present disclosure provides compositions useful for the prevention and/or treatment of blepharitis, methods for preventing or treating blepharitis in a subject, and methods for preparing compositions useful for the prevention and/or treatment of blepharitis.

In some embodiments, the disclosure may provide compositions that include verbascoside, oligopeptide-10, and sulfonated shale oil.

In some embodiments, the disclosure may provide methods for preventing or treating blepharitis in a subject, the methods including topically applying an effective amount of a composition that includes verbascoside in a concentration of $1.0 \times 10^{-4}$ to 1.0 percent by weight, oligopeptide-10 in a concentration of $5.0 \times 10^{-6}$ to 0.50 percent by weight, and sulfonated shale oil in a concentration of $1.0 \times 10^{-4}$ to 2.0 percent by weight.

In some embodiments, the disclosure may provide methods for preparing compositions effective for treating or preventing blepharitis, the methods including preparing a concentrated mixture that includes 0.001 to 10 weight percent verbascoside, 0.0001 to 0.5 weight percent oligopeptide-10, and 0.001 to 20 weight percent sulfonated shale oil; and then combining the concentrated mixture with one or more cosmetically acceptable excipients.

The features, functions, and advantages of the disclosure may be achieved independently in various embodiments, or may be combined in yet other embodiments, further details of which can be seen with reference to the following description.

DETAILED DESCRIPTION

The present disclosure is directed to compositions that possess unexpected efficacy in treating or preventing the symptoms of blepharitis. In particular, the present disclosure is directed to compositions containing a combination of verbascoside, oligopeptide-10, and sulfonated shale oil. In some embodiments, these compositions are formulated as cosmetic compositions, which unlike traditional cosmetics, do not cause or exacerbate the symptoms associated with blepharitis.

Verbascoside is a naturally occurring phenylpropanoid glycoside (PPG) that is a water-soluble derivative of phenylpropanoid (PP), and has the chemical formula:

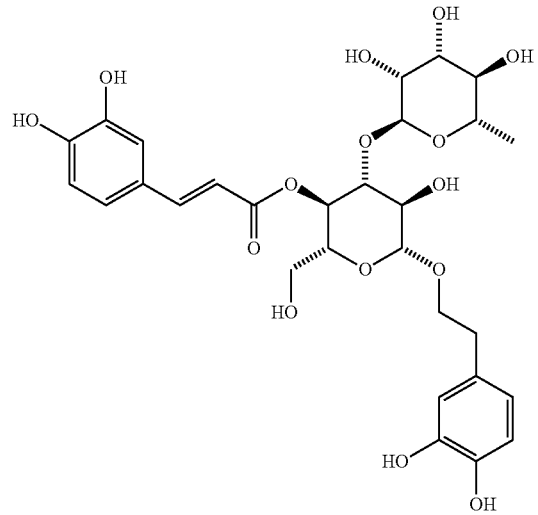

Verbascoside

Verbascoside, also known as acteoside or kusaginin, exhibits anti-inflammatory and anti-bacterial activity, and may be obtained by isolation or extraction from any of a variety of medicinal plants that contain the compound, for example in species of all the families of the Lamiales order. In particular, verbascoside may be obtained from the leaves of the *Buddleja cordata* tree by drying, grinding, and extracting the leaves with hexane and methanol. The methanolic portion of the extract may be evaporated to obtain a crude syrup that may be further treated to produce a verbascoside amorphous powder. Alternatively or in addition, verbascoside may be purchased from a number of commercial suppliers (SIGMA-ALDRICH, ADOOQ BIOSCIENCE, among others).

The commercially-available Oligopeptide-10 (made by HELIX BIOMEDIX and distributed by GRANT INDUSTRIES, NJ) is a proprietary oligopeptide having anti-microbial properties (see U.S. Pat. No. 7,381,704, hereby incorporated by reference). Oligopeptide 10 may be stable over a broad range of temperatures and pH values.

Shale oil refers to oil that is extracted from fissures in shale, typically by pyrolysis or thermal extraction. Shale oils are useful as anti-inflammatory, anti-bacterial, and/or anti-mycotic agents when applied topically, and sulfonation of shale oil may render it partially or completely water-soluble. Although any sulfonated shale oil suitable for topical use is appropriate for the present compositions, pale sulfonate shale oil (or PSSO) may be particularly advantageous. Appropriate sulfonated shale oils for the purposes of the present disclosure may be obtained commercially from ICHTHYOL GESELLSCHAFT (Hamburg, Germany), in particular a dark sulfonated shale oil (ICHTHAMMOL®) and a light-colored pale sulfonated shale oil (ICHTHYOL® PALE).

Although each of verbascoside, oligopeptide-10, and sulfonated shale oil possess anti-inflammatory properties, the combination of all three in a single composition confers upon that composition beneficial anti-inflammatory and anti-bacterial properties that are greater than that of any individual component. That is, the combination exhibits a synergistic effect, where the joint action of the three components when combined is greater than the sum of their individual effects. This is particularly true with respect to the treatment or prevention of blepharitis, where the application of all three components provides improved blepharitis prevention and treatment when compared to the results of the administration of verbascoside, sulfonated shale oil, or oligopeptide-10 alone.

The verbascoside, oligopeptide-10, and sulfonated shale oil may be incorporated into the compositions of the present disclosure in any therapeutically effective ratio or concentration. In one embodiment, the compositions of the present disclosure include verbascoside in a concentration of $1.0 \times 10^{-4}$ to 1.0 percent by weight; include oligopeptide-10 in a concentration of $5.0 \times 10^{-6}$ to 0.50 percent by weight; and include sulfonated shale oil in a concentration of $1.0 \times 10^{-4}$ to 2.0 percent by weight.

The verbascoside, oligopeptide-10, and sulfonated shale oil may be incorporated into the compositions of the present disclosure in any suitable form. In one embodiment of the present compositions, one or more of the verbascoside, oligopeptide-10, and sulfonated shale oil components may be present in the composition in an encapsulated form, that is coated by or enclosed within another substance in order to regulate the release of the free components over time, or to protect and stabilize the components with respect to environmental conditions. Various methods of encapsulation of compositions, such as cosmetic compositions, are well known.

Where one or more components of the present compositions are encapsulated, the encapsulated components may be configured to be released immediately, released over time, or a mixture of immediate- and sustained-release encapsulations. Alternatively, or in addition, encapsulation of one or more components may be used to stabilize the components with respect to exposure to oxygen, light, heat, or other adverse conditions. For example, one or more components may be encapsulated in such a way that the free component is released at body temperature, but stabilized at less than body temperatures.

Complex S

In an illustrative method of preparing the compositions of the present disclosure, the verbascoside, oligopeptide-10, and sulfonated shale oil components, optionally in combination with one or more additional components, may be precombined to create a relatively concentrated mixture herein referred to as Complex S. The Complex S mixture may then be incorporated into compositions of the present disclosure in the desired concentration. In one embodiment of the present disclosure, Complex S is incorporated into compositions of the present disclosure to a concentration of about 0.0001% to 5% by weight. Alternatively, the desired active ingredients of Complex may be added individually or in subcombinations, provided that the active ingredients are present in combination in the final composition.

In addition to verbascoside, oligopeptide-10, and sulfonated shale oil, the Complex S mixture may include one or more additional active ingredients. By active ingredient is meant a substance, extract, or compound that exhibits one or more of anti-bacterial, anti-microbial, and anti-inflammatory activity, or that enhances the anti-bacterial, anti-microbial, or anti-inflammatory activity of another ingredient, particularly when applied topically. Selected active ingredients that may be combined in Complex S include, but are not limited to, neem oil, turmeric extract, willowbark extract, *Euphreisia officinalis* extract, *Cipadessa baccifera* extract, black seed oil, and anise extract, among others. Representative and exemplary ingredients for the Complex S mixture as an aqueous composition, and a range of ingredient concentrations, are provided in Table 1.

TABLE 1

Exemplary Ingredients of Complex S

| Ingredients | % W/W |
| --- | --- |
| Verbascoside | 0.001-10 |
| Oligopeptide-10 | 0.0001-0.5 |
| Shale Oil | 0.001-20 |
| Neem Oil | 0-20 |
| Tumeric Extract | 0-10 |
| Willowbark Extract | 0-15 |
| *Euphrasia officinalis* Extract | 0-25 |
| Black Seed Oil | 0-1.0 |
| Anise Extract | 0-1.0 |
| Dionized water | qs to 100% |

Compositions

The Complex S mixture may be used to prepare a variety of compositions for topical application useful for treating and/or preventing skin irritations caused by bacterial infection. In one aspect of the present disclosure, the compositions of the present disclosure are cosmetic compositions useful for the prevention and/or treatment of blepharitis.

In addition to active ingredients, as set out above, the compositions of the present disclosure may additionally include one or more cosmetic excipients. A cosmetic excipient, as used herein, may be any natural or synthetic substance formulated alongside the active ingredient of a composition that is included for the purpose of, for example, long-term stabilization, bulking up solid compositions, diluting those compositions that contain potent active ingredients, facilitating flowability, and reducing aggregation, among other purposes.

Selected cosmetic excipients may include solvents, waxes, oils, lipids, fatty alcohols, colorants, flavoring, fragrances, sequestrants, humectants, thickening agents, emulsifiers, emollients, adsorbing agents, preservatives, vitamins, antioxidants, pH modifiers, texturizing agents, silicas, and other ingredients usually used in cosmetic products, or combinations thereof.

When present, the organic solvents of the present compositions may include any organic solvent that is suitable for use in cosmetic products, such as aliphatic hydrocarbons having 12-22 carbon atoms, including isoparaffins like isohexane and isododecane; or diols, such as 1,3-butylene glycol.

When present, the waxes of the present compositions may include one or more of candelilla wax, carnauba wax, beeswax, ceresine, microcrystalline wax, paraffin wax, silicon wax, and polyethylene wax, among others. Alternatively, or in addition, the present compositions may include one or more silicones or silicone derivatives, such as cyclomethicone, and dimethicone, among others.

When present, suitable colorants may include for example iron oxides, chromium oxide and/or hydroxide, blue and pink ultramarine, manganese violet, titanium dioxide, pearlescent pigments based on mica or bismuth oxychloride substrates, carmin, lakes and pigments based on organic colorants, among others.

Additional suitable cosmetically acceptable excipients may include glycerine, xanthan gum, talc, mica, kaolin, unmodified clays, zinc oxide, calcium carbonate, magnesium carbonate phosphate, calcium bisulfate, starch and its derivatives, nylon, polyethylene, and acrylic (co)polymers, among others. Such excipients may comprise the balance of the total composition as further illustrated by the examples provided below. The individual concentrations of the components of the disclosed compositions may depend upon the type of composition being produced, and its intended use. For example, the composition may be formulated to be a liquid, semiliquid, paste, or cake. Individual concentrations of suitable excipients are listed in the examples, but these individual concentrations may be modified in either direction, to a higher or lower percentage, as needed.

The cosmetic compositions of the present disclosure may be formulated to function as lotions, creams, eye pencils, eye shadows, hydroalcoholic liquids or sprays, cosmetic primers, cosmetic sera, mascaras, eyeliners, and single phase liquids or sprays, among others. These cosmetic compositions can be applied topically on any exposed skin surface that could be affected by blepharitis including, but not limited to, eyelids and the areas surrounding each of the eyes.

Prevention/Treatment of Blepharitis

The compositions of the present disclosure may be highly useful for preventing and/or treating blepharitis in a subject. That is, the compositions may be useful for preventing blepharitis in a subject that does not yet manifest the symptoms of blepharitis, and may be additionally and advantageously useful for the treatment of blepharitis in a subject already suffering from that condition.

The prevention or treatment of blepharitis in a subject may include a method of topically applying a therapeutically effective amount of a composition comprising verbascoside, oligopeptide-10, and sulfonated shale oil to the subject. Topically applying the composition may include topically applying the composition to an affected skin area of the subject. In one aspect of the present disclosure, the composition may be a cosmetic composition.

The composition may be effective for preventing and/or treating blepharitis where verbascoside is present in the composition in a concentration of $1.0 \times 10^{-4}$ to 1.0 percent by weight; oligopeptide-10 is present in the composition in a concentration of $5.0 \times 10^{-6}$ to 0.50 percent by weight; and sulfonated shale oil is present in the composition in a concentration of $1.0 \times 10^{-4}$ to 2.0 percent by weight.

The application of the compositions of the present disclosure may be helpful for both preventing the presence of blepharitis and treating the severity of blepharitis. In particular, application of the present compositions may help alleviate one or more symptoms of blepharitis, resulting in for example a reduction of sebum production, a reduction of bacterial growth, and the unclogging of pores in the affected area.

Preparation of the Compositions

The compositions of the present disclosure may be prepared in any convenient fashion, but may conveniently be prepared by first formulating a relatively more concentrated Complex S mixture, which may optionally include one or more additional active ingredients, and then combining an aliquot of the Complex S mixture with the desired cosmetic excipients to form a composition having the desired appearance, consistency, fragrance, and color.

Although the preparation of selected embodiments of the compositions of the present disclosure are described in the examples below, these examples are provided only to illustrate selected aspects of the disclosure, and are not intended to limit the scope of the disclosure, which is defined by the claims appended hereto.

EXAMPLES

The abbreviation "qs" stands for "quantity sufficient," and may refer to an amount necessary to confer the desired effect (as in the case of fragrances or preservatives), or an amount necessary for the sum of the ingredients concentrations to equal 100% w/w (as in the case of deionized water).

Example 1. Preparation of Complex S

Although suitable compositions may be prepared by using similar concentrations of the various components of Complex S individually, or in subcombinations, it may be convenient to prepare an initial Complex S mixture, and then to use a portion of the Complex S mixture in formulating each desired composition.

An illustrative Complex S mixture is described below in Table 2:

TABLE 2

| Illustrative Complex S Formulation | |
|---|---|
| Ingredients | % W/W |
| Verbascoside | 10.00 |
| Oligopeptide-10 | 0.50 |
| Shale Oil | 20.00 |
| Neem Oil | 20.00 |
| Turmeric Extract | 10.00 |
| Willowbark Extract | 15.00 |
| *Euphrasia officinalis* Extract (in H$_2$O) | qs to 100 |
| Black Seed Oil | 1.00 |
| Anise Extract | 1.00 |

The Complex S formulation may be prepared as an aqueous solution. In one aspect of the present disclosure, the *Euphrasia officinalis* extract is provided as a solution in deionized water, and an amount of *Euphrasia officinalis* is used sufficient to obtain a desired concentration of the Complex S components.

The concentrations provided for the above illustrative Complex S mixture are suitable for incorporation in a cosmetic composition at a concentration of Complex S of about 5% or less. Higher percentages, or the use of more concentrated active ingredients, may remain effective at preventing and/or treating blepharitis, but may be more likely to cause skin irritation.

Example 2 Preparation of an Oil-in-Water Lotion Formulation

|  | Ingredient | % (w/w) |
|---|---|---|
| Phase A | Deionized Water | qs |
|  | 1,3 Butylene Glycol | 5.00 |
|  | Glycerine | 3.00 |
|  | Disodium EDTA | 0.10 |
|  | Xanthan Gum | 0.30 |
| Phase B | Capric/capric triglyceride | 10.00 |
|  | Octyl palmitate | 5.00 |
|  | Cetyl Alcohol | 1.00 |
|  | Dimethicone (350 cks) | 1.00 |
|  | PEG 100 Stearate | 3.00 |
|  | Stearyl alcohol | 1.00 |
|  | Tocopheryl Acetate | 0.50 |
|  | Salicylic Acid (as applicable) | 0.1% to 20% |
| Phase C | Complex S | 0.0001 to 5% |
|  | Retinol or Retinol derivatives (as applicable) | 0.01% to 0.25% |
| Phase D | Fragrance | qs |
| Phase E | Preservative | qs |

Phase A is prepared by adding the butylene glycol, glycerine, and disodium EDTA to a mixture of the remaining ingredients in sufficient water. The resulting combination is heated to 80° C.

Phase B is prepared by mixing the ingredients together and heating the mixture to 80° C. Phase B is then added to Phase A while mixing. The resulting mixture is cooled to 35° C. while being mixed. The ingredients of Phases C, D, and E are then combined with the mixture to yield the desired lotion formulation.

Example 3. Preparation of an Oil-in-Water Cream Formulation

|  | Ingredient | % (w/w) |
|---|---|---|
| Phase A | Deionized Water | qs |
|  | 1,3 Butylene Glycol | 5.00 |
|  | Glycerine | 3.00 |
|  | Disodium EDTA | 0.10 |
|  | Xanthan Gum | 0.30 |
| Phase B | Capric/capric triglyceride | 10.00 |
|  | Octyl palmitate | 5.00 |
|  | Cetyl Alcohol | 2.00 |
|  | Stearyl alcohol | 1.00 |
|  | Glyceryl Stearate | 2.50 |
|  | PEG 100 Stearate | 3.00 |
|  | Tocopheryl Acetate | 0.50 |
| Phase C | Complex S | 0.0001 to 5% |
|  | Retinol or Retinol derivatives (as applicable) | 0.01% to 0.25% |
| Phase D | Fragrance | qs |
| Phase E | Preservative | qs |
| Phase F | Colorants | qs |

Phase A is prepared by adding the butylene glycol, glycerine and disodium EDTA to water and the other ingredients of Phase A. The resulting combination is then heated to 80° C.

Phase B is prepared by mixing the ingredients together and heating the resulting mixture to 80° C. Phase B is added to Phase A with mixing, and the entire combined mixture is cooled to 35° C. while being mixed. The ingredients of phases D, E, and F are then added.

Example 4. Preparation of a Water-in-Oil Lotion Formulation

|  | Ingredient | % (w/w) |
|---|---|---|
| Phase A | Deionized Water | qs |
|  | 1,3 Butylene Glycol | 5.00 |
|  | Glycerine | 3.00 |
|  | Disodium EDTA | 0.10 |
|  | Sodium Chloride | 2.00 |
| Phase B | Dimethicone and polysilicone-11 | 10.00 |
|  | Octyl palmititate | 5.00 |
|  | Dimethicone/and PEG/PPG 18/18 Dimethicone | 3.00 |
|  | PEG-10 Dimethicone | 3.00 |
|  | Beeswax | 2.50 |
|  | Tocopheryl Acetate | 0.50 |
| Phase C | Complex S | 0.0001% to 5% |
|  | Retinol or Retinol derivatives (as applicable) | 0.01% to 0.25% |
| Phase D | Fragrance | qs |
| Phase E | Preservative | qs |
| Phase F | Colorants | qs |

Phase A is prepared by adding the butylene glycol, glycerine, sodium chloride, sodium borate, and disodium EDTA to a mixture of water and the remaining components. The resulting combination is then heated to 80° C.

Phase B is prepared by mixing the ingredients together and heating the resulting mixture to 80° C.

Phase B is added to Phase A with mixing. The entire resulting mixture is then cooled to 35° C. while being mixed. The ingredients of Phases C, D, E, and F ingredients are then added.

Example 5 Preparation of a Composition Suitable for an Eye Pencil (A)

|  | Ingredient | % (w/w) |
|---|---|---|
| Phase A | Rhus Succedanea Fruit Wax | qs |
|  | Hydrogenated Vegetable Oil | 7.50 |
|  | Hydrogenated Palm Kernel Glycerides | 7.50 |
|  | Stearic Acid | 5.00 |
|  | Copernicia Cerifera (Carnauba) Wax | 4.00 |
|  | Hydrogenated Coco-Glycerides | 3.00 |
|  | Beeswax (Cera Alba) | 2.00 |
|  | Caprylic/Capric Triglyceride | 2.00 |
|  | Coco-Caprylate/Caprate | 2.00 |
|  | Tristearin | 2.00 |
|  | Hydrogenated Palm Glycerides | 2.00 |
|  | Talc | 1.00 |
|  | Behenyl Behenate | 0.50 |
|  | Preservative | qs |
|  | Tocopheryl Acetate | <1% |
|  | *Aloe Barbadensis* Leaf Extract | 0.50 |
|  | Isopropyl Myristate | 0.50 |
|  | Isopropyl Palmitate | 0.50 |
|  | Iron Oxides CI 77499 | 37.50 |
|  | Ferric Ammonium Ferrocyanide CI 77510 | 2.00 |

-continued

| Ingredient | % (w/w) |
|---|---|
| Ultramarines CI 77007 | 2.00 |
| Carmine CI 75470 | 0.50 |
| Complex S | 0.0001% to 5% |

All the components of Phase A are combined by mixing until uniform. The resulting mixture is then formed into suitable shape for application to a user's eye.

Example 6. Preparation of a Composition Suitable for an Eye Pencil (B)

| | Ingredient | % (w/w) |
|---|---|---|
| Phase A | Beeswax | qs |
| | Coco Caprylate/Caprate | 1.00 |
| | D&C Black #2 | 10.00 |
| | Carnauba Wax (Copernicia Cerifera (Carnauba) Wax) | 2.00 |
| | Euphorbia Cerifera (Candelilla) Wax | 3.00 |
| | Microcrystalline Wax | 4.00 |
| | Polyethylene | 2.00 |
| | Talc | 7.00 |
| | Preservative | qs |
| | Complex S | 0.0001% to 5% |
| | Fragrance | qs |
| | Colorants | qs |

All the components of Phase A are combined, and the resulting mixture is heated to 95° C. After heating, the mixture is mixed until uniform and then cooled to room temperature. The resulting composition is then formed into a suitable shape for application to a user's eye.

Example 7. Preparation of a Composition Suitable for an Eye Shadow

| | Ingredient | % (w/w) |
|---|---|---|
| Phase A | Talc | qs |
| | Zinc Stearate | 7.00 |
| | Calcium Silicate | 0.10 |
| | Silica | 5.00 |
| | Red Iron Oxide | 0.30 |
| | Yellow Iron Oxide | 1.00 |
| | Black Iron Oxide | 0.10 |
| | Mica (and) Titanium Dioxide | 15.00 |
| | Preservative | qs |
| | Complex S | 0.0001% to 5% |
| | Coco Caprylate/Caprate | 5.00 |
| | Isopropyl Isostearate | 3.00 |
| | Fragrance | qs |
| | Colorants | qs |

The eye shadow is formed by mixing all components of Phase A together until uniform and forming the mixed components into a suitable shape for application to a user's eye.

Example 8. Preparation of a Composition Suitable for a Hydroalcoholic Liquid or Spray

| | Ingredient | % (w/w) |
|---|---|---|
| Phase A | Deionized Water | qs |
| | Denatured Alcohol | 20.00 |
| | 1,3 Butylene Glycol | 5.00 |
| | Glycerine | 3.00 |
| Phase B | Complex S | 0.0001% to 5% |
| Phase C | Fragrance | qs |
| Phase D | Preservative | qs |
| Phase E | Colorants | qs |

Phase A is prepared by combining all Phase A components. The Phase B, C, D, and E components are then mixed together, and the resulting mixture is then combined with Phase A.

Example 9. Preparation of a Cosmetic Primer

| | Ingredient | % (w/w) |
|---|---|---|
| Phase A | Deionized Water | qs |
| | 1,3 Butylene Glycol | 5.00 |
| | Glycerine | 3.00 |
| | Decyl glucoside | 0.10 |
| | Polysorbate-20 | 0.10 |
| | Carbomer | 0.20 |
| | Hydroxy ethylcellulose | 0.20 |
| Phase B | Dimethicone (and) Polysilicone-11 (and) Butylene Glycol (and) Water (and) Decyl Glucoside (SiW-066) | 15.00 |
| | Isododecane (and) Trimethylsiloxysilicate (and) Water (and) Propanediol (and) Decyl Glucoside (SiW-MQIZ) | 10.00 |
| | Capric/Capric triglyceride | 1.00 |
| | Ammonium Acryloyldimethyltaurate/VP Copolymer (Aristoflex AVC) | 0.50 |
| Phase C | Preservative | qs |
| Phase D | Complex S | 0.0001% to 5% |

Phase A is prepared by combining all Phase A components. The Phase B, C, and D components are mixed together, and the resulting mixture is then combined with Phase A.

Example 10. Preparation of a Mascara Formulation

| | Ingredient | % (w/w) |
|---|---|---|
| Phase A | Deionized Water | qs |
| | Hydroxyethylcellulose | 0.75 |
| | Black iron oxide | 10.00 |
| Phase B | Glyceryl Stearate | 4.00 |
| | Carnauba Wax (Copernicia Cerifera (Carnauba) Wax) | 5.00 |
| | Stearic Acid | 4.00 |
| | Propylene Glycol Stearate | 2.00 |
| | Beeswax | 4.00 |
| | C18-36 Triglyceride | 0.40 |
| | Paraffin Wax (Paraffin) | 1.00 |
| Phase D | Acrylates Copolymer | 10.00 |
| Phase E | Silica Beads (Silica) | 2.00 |
| | Complex S | 0.0001 to 5% |
| | DI Water | 4.00 |

Phase A is prepared by all of the Phase A components, and then heating the combined mixture to 85° C. Phase B is prepared by mixing the Phase B components together, and heating the resulting mixture to 85-90° C.

While warm, Phase B is added to Phase A with mixing. The combined mixture is then cooled to 35° C. with additional mixing. The Phase C, D, and E, components are then added.

Example 11. Preparation of a Waterproof Mascara Formulation Containing Iron Oxide

|  | Ingredient | % (w/w) |
| --- | --- | --- |
| Phase A | Petroleum Distillates | qs |
|  | Tall Oil Glycerides | 5.00 |
|  | Black iron oxide | 10.00 |
|  | Ozokerite Wax (Ozokerite) | 5.00 |
|  | Carnauba Wax (Copernicia Cerifera (Carnauba) Wax) | 6.00 |
|  | Ethylcellulose | 0.60 |
|  | Distinctive Gel ID (Quaternium-90 Bentonite (and) Isododecane (and) Propylene Carbonate | 15.00 |
|  | Beeswax | 2.00 |
|  | Kaolin | 5.00 |
|  | Preservative | qs |
|  | Silica | 0.30 |
|  | Complex S | 0.0001% to 5% |

Phase A is prepared by combining all Phase A components and heating the resulting mixture to 95° C. Phase A is mixed until uniform, while hot, then cooled to room temperature and formed into a suitable shape for application to a user's eye.

Example 12. Preparation of an Eyeliner Formulation Containing Iron Oxide

|  | Ingredient | % (w/w) |
| --- | --- | --- |
| Phase A | DI Water | qs |
|  | PVP | 3.00 |
|  | Black iron oxide | 8.00 |
|  | Polyester - 5 | 5.00 |
|  | Preservative | qs |
|  | Acrylates Copolymer | 5.00 |
|  | Complex S | 0.0001% to 5% |
|  | Fragrance | qs |
|  | Colorants | qs |

Phase A is prepared by combining all Phase A components and heating the resulting mixture to 85° C. The components are mixed while hot until uniform, then cooled to room temperature and formed into a suitable shape for application to a user's eye.

Example 13. Preparation of a Mascara Formulation Containing Iron Oxide

|  | Ingredient | % (w/w) |
| --- | --- | --- |
| Phase A | Deionized Water | qs |
|  | Hydroxyethylcellulose | 0.75 |
|  | Black iron oxide | 10.00 |
|  | Tromethamine 40% | 5.69 |
|  | Preservative | qs |
|  | Polyester - 5 | 5.00 |

-continued

|  | Ingredient | % (w/w) |
| --- | --- | --- |
| Phase B | Glyceryl Stearate | 4.00 |
|  | Carnauba Wax (Copernicia Cerifera (Carnauba) Wax) | 5.00 |
|  | Stearic Acid | 4.00 |
|  | Propylene Glycol Stearate | 2.00 |
|  | Beeswax | 4.00 |
|  | C18-36 Triglyceride | 0.40 |
|  | Paraffin Wax (Paraffin) | 1.00 |
|  | Salicylic Acid (as applicable) | 0.1% to 20% |
| Phase D | Acrylates Copolymer | 10.00 |
| Phase E | Silica | 0.20 |
|  | DI Water | 4.00 |
|  | Complex S | 0.0001% to 5% |

Phase A is prepared by combining all of the Phase A components and heating the combined mixture to 85° C. Next, the Phase B ingredients are mixed together and heated to 85-90° C. While warm, the Phase B mixture is added to Phase A with mixing. While continuing to mix the combined mixture, it is cooled to 35° C. The Phase C, D, and E components are then added to the mixture.

Example 14. Preparation of a Single Phase Cosmetic Liquid or Spray

|  | Ingredient | % (w/w) |
| --- | --- | --- |
| Phase A | Deionized Water | qs |
|  | 1,3 Butylene Glycol | 5.00 |
|  | Glycerine | 3.00 |
|  | Complex S | 0.0001% to 5% |
| Phase B | Preservative | qs |

Phase A is prepared by combining all Phase A ingredients. The ingredients are mixed until uniform, and then added to the Phase B component.

Example 20. Preparation of Makeup Remover Wipes

|  | Ingredient | % (w/w) |
| --- | --- | --- |
| Phase A | Water | qs |
|  | Complex S | 0.0001% to 5% |
|  | Methyl glucose sesquistearate | 1.00 |
|  | PEG 20 Methyl glucose sesquistearate | 0.80 |
| Phase B | Isohexadecane | 10.00 |
|  | Hexylene Glycol | 7.00 |
|  | Dimethicone | 3.00 |
|  | Isopropyl palm itate | 1.00 |
|  | Trisiloxane | 1.00 |
|  | Tocopherol | 0.20 |
| Phase C | Preservative | qs |

Phase A is prepared by combining all Phase A ingredients and mixing until the combination is uniform. Phase A is then combined with the Phase B and C ingredients and again mixed until uniform. A quantity of porous sheets suitable for use as makeup remover wipes are then impregnated with the resulting mixture.

Although the compositions and methods of the present disclosure have been shown and described with reference to the foregoing operational principles and preferred embodiments, it will be apparent to those skilled in the art that various changes in form and detail may be made without departing from the spirit and scope of the disclosure. The present invention is intended to embrace all such alternatives, modifications and variances that fall within the scope of the appended claims.

It is believed that the disclosure set forth above may encompass multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A composition comprising verbascoside, oligopeptide-10, and sulfonated shale oil, wherein the verbascoside is present in the composition in a concentration of $1.0 \times 10^{-4}$ to 1.0 percent by weight, the oligopeptide-10 is present in the composition in a concentration of $5.0 \times 10^{-6}$ to 0.50 percent by weight, and the sulfonated shale oil is present in the composition in a concentration of $1.0 \times 10^{-4}$ to 2.0 percent by weight.

2. The composition of claim 1, wherein verbascoside and shale oil are present in the composition in a ratio of one part verbascoside to two parts shale oil by weight.

3. The composition of claim 1, wherein verbascoside and oligopeptide-10 are present in the composition in a ratio of 20 parts verbascoside to one part oligopeptide-10 by weight.

4. The composition of claim 1, further comprising one or more additional active ingredients selected from neem oil, turmeric extract, willowbark extract, *Euphrasia officinalis* extract, black seed oil, and anise extract.

5. The composition of claim 1, wherein verbascoside is present in the composition in a concentration of about 0.5 percent by weight; oligopeptide-10 is present in the composition in a concentration of about 0.025 percent by weight; and sulfonated shale oil is present in a concentration of about 1.0 percent by weight.

6. The composition of claim 1, wherein the composition is a cosmetic composition, further comprising one or more cosmetically acceptable excipients.

7. The composition of claim 6, wherein the one or more excipients are selected from the group consisting of: solvents, sequestrants, humectants, thickening agents, emulsifiers, emollients, adsorbing agents, preservatives, fragrances, antioxidants, pH modifiers, texturizing agents, and combinations thereof.

8. The composition of claim 6, wherein the composition is an eye pencil, an eye shadow, an eye liner, a mascara, a cosmetic primer, or a cosmetic serum.

9. The composition of claim 1, wherein the composition is a lotion, a cream, or a liquid.

10. The composition of claim 1, wherein the composition is dispersed on or in an absorbent substrate.

11. A composition for treating or preventing blepharitis, comprising:
   a precombined concentrated mixture of active ingredients including verbascoside, oligopeptide-10, and sulfonated shale oil; and
   at least one cosmetic excipient;
   wherein the precombined concentrated mixture is present in the composition in a concentration of 0.0001% to 5% by weight; and wherein the verbascoside is present in the composition in a concentration of $1.0 \times 10^{-4}$ to 1.0 percent by weight, the oligopeptide-10 is present in the composition in a concentration of $5.0 \times 10^{-6}$ to 0.50 percent by weight, and the sulfonated shale oil is present in the composition in a concentration of $1.0 \times 10^{-4}$ to 2.0 percent by weight.

12. The composition of claim 11, further comprising one or more additional active ingredients selected from neem oil, turmeric extract, willowbark extract, *Euphrasia officinalis* extract, black seed oil, and anise extract.

13. The composition of claim 11, wherein verbascoside is present in the composition in a concentration of about 0.5 percent by weight; oligopeptide-10 is present in the composition in a concentration of about 0.025 percent by weight; and sulfonated shale oil is present in a concentration of about 1.0 percent by weight.

14. The composition of claim 11, wherein the composition is an eye pencil, an eye shadow, an eye liner, a mascara, a cosmetic primer, or a cosmetic serum.

15. The composition of claim 11, wherein the composition is a lotion, a cream, or a liquid.

16. An eye makeup formulation, comprising:
   a precombined concentrated mixture of active ingredients for treating or preventing blepharitis, including verbascoside, oligopeptide-10, and sulfonated shale oil collectively present in the formulation in a concentration of 0.0001% to 5% by weight;
   a wax; and
   a colorant; wherein the verbascoside is present in the composition in a concentration of $1.0 \times 10^{-4}$ to 1.0 percent by weight, the oligopeptide-10 is present in the composition in a concentration of $5.0 \times 10^{-6}$ to 0.50 percent by weight, and the sulfonated shale oil is present in the composition in a concentration of $1.0 \times 10^{-4}$ to 2.0 percent by weight.

17. The formulation of claim 16, further comprising one or more additional active ingredients selected from neem oil, turmeric extract, willowbark extract, *Euphrasia officinalis* extract, black seed oil, and anise extract.

18. The formulation of claim 16, wherein the colorant is an iron oxide.

* * * * *